United States Patent [19]

Kim et al.

[11] Patent Number: 5,686,277
[45] Date of Patent: Nov. 11, 1997

[54] FERMENTATION PROCESS FOR PREPARING XYLITOL USING MUTANT CELLS

[75] Inventors: Sang Yong Kim, Kyungki-Do; Deok Kun Oh, Cheonju; Jin Hwan Choi, Seoul; Soo Eun Kim, Koyang, all of Rep. of Korea

[73] Assignees: Tong Yang Confectionery Corp., Seoul; Bolak Co., Ltd., Kyungki-Do, both of Rep. of Korea

[21] Appl. No.: 736,622

[22] Filed: Oct. 24, 1996

[30] Foreign Application Priority Data

Oct. 27, 1995 [KR] Rep. of Korea ............ 95-37516

[51] Int. Cl.$^6$ ............... C12N 1/16; C12P 7/18
[52] U.S. Cl. ............... 435/158; 435/254.22; 435/255.4; 435/921
[58] Field of Search ............... 435/158, 255.4, 435/921, 254.22

[56] References Cited

U.S. PATENT DOCUMENTS

| | | | |
|---|---|---|---|
| 3,619,369 | 11/1971 | Onishi et al. | 435/158 |
| 3,627,630 | 12/1971 | Jafee et al. | 435/158 |
| 4,511,656 | 4/1985 | Gong | 435/161 |
| 5,081,026 | 1/1992 | Heikkila et al. | 435/158 |
| 5,096,820 | 3/1992 | Leleu et al. | 435/158 |

OTHER PUBLICATIONS

Biotechnology Letters, vol. 13, No. 4 (1991) pp. 281–286; V. Meyrial et al.: *Xylitol Production From D–Xylose by Candida Guillermondii: Fermentation Behaviour.*

Applied Microbiology and Biotechnology (1994), 19:256–260; Peter M. Bruinenberg et al.: *NADH–linked aldose reductase: the key to anarobic alcoholic fermentation of xylose by yeasts.*

Biotechnology Letters, vol. 11, No. 2, (1989) pp. 131–136, J.C. du Preez et al.: d–Xylose Fermentation by Candida Shehatae and Pichia Stipitis at Low Dissolved Oxygen Levels in Fed–Batch Cultures.

Biotechnology Letters, vol. 10, No. 12, (1988) pp. 901–906; J.C. du Preez et al.: The Relation Between Redox Potential and D–Xylose Fermentation by Candida Shehatae and Pichia Stipitis.

Journal of General Microbiology, vol. 135, (1989) pp. 2791–2798, Carina Van Zyl et al.: D–Xylose Utilization by Saccharomyces cerevisiae.

Applied and Environmental Microbiology (1993) pp. 1049–1053; Jie Xu et al.: Effect of Nystatin on the Metabolism of Xylitol and Xylose by Pachysolen tannophilus.

Applied Microbiology and Biotechnology, (1991), 36:375–378; Z. Kossaczka et al.: D–Xylose metabolism in Aureobasidium pullulans: effects of aeration and vitamins.

Applied Microbiology and Biotechnology, (1993), 38:776–783; Peter Koetter et al.: Xylose fermentation by Saccharomyces cerevisiae.

Biotechnology Letters, vol. 12, No. 1, pp. 57–60 (1990), J.R. Kastner et al.: *Simultaneous Fermentation of D–Xylose and Gluciose by Candida shehatae.*

Enzyme Microb. Technol., 1988, vol. 10, Feb., Hung Lee et al.: *Effect of biotin limitation on the conversion of xylose to ethanol and xylitol by Pachysolen tannophilus and Candida guilliermondii.*

Primary Examiner—Herbert J. Lilling
Attorney, Agent, or Firm—Kenyon & Kenyon

[57] ABSTRACT

The present invention relates to a fermentation process for preparing xylitol with high productivity using novel mutant cells of *Candida parapsilosis*, more specifically, for preparing xylitol under optimal fermentation conditions for maximum xylitol production by optimizing the composition of medium containing xylose and the environmental conditions of culture such as pH, temperature and DO concentration, anal controlling the concentration of mutant cells.

5 Claims, No Drawings

FERMENTATION PROCESS FOR PREPARING XYLITOL USING MUTANT CELLS

BACKGROUND OF THE INVENTION

1. Field of the Invention

The present invention relates to a fermentation process for preparing xylitol with high productivity using novel mutant cells of *Candida parapsilosis*, more specifically, for preparing xylitol under optimal fermentation conditions for maximum xylitol production by optimizing the composition of medium containing xylose and the environmental conditions of culture such as pH, temperature and DO concentration, and controlling the concentration of mutant cells.

2. Description of Prior Art

Xylitol, a five carbon sugar alcohol, has anticariogenic property which does not cause acid formation and a sweetness equal to sucrose and can replace sucrose on a weight—weight basis. Xylitol has substantially lower viscosity and negative heat effect when dissolved in a solution. With these properties, xylitol has found increasing use in the food industries, especially in confectionery. Xylitol may be also used clinically as a sugar substitute for treatment of diabetes or glucose-6-phosphate dehydrogenase deficient population since insulin is not needed for its digestion.

Xylitol is a normal intermediary product of carbohydrate metabolism in human and animals. It is also widely distributed in the plant especially in certain fruits and vegetables. However, the small amounts present in these sources render its quantitative extraction difficult and uneconomical.

Conventionally, xylitol has been chemically prepared by hydrogenation reaction from xylose in the presence of metal catalyst. However, such hydrogenation reaction is dangerous xylitol since it requires plenty of organic solvent under high temperature and pressure. Furthermore, it does not show good yield due to the difficulties in separation and purification of xylitol from the reaction mixture.

To overcome such drawbacks of chemical preparation method, the biological fermenation process for preparing xylitol has been researched. The fermentation process for preparing xylitol using yeast speices from the medium containing xylose or hemicellulose hydrolysate having xylose has been disclosed. Especially, *Candida blankii, Candida guilliermondii, Candida tropicalis, Candida utilis, Saccharomyces bailii, Saccharomyces rouxii, Saccharomyces uvarium* and *Schizosaccharomyces pombe* have been known as the microorganism producing xylitol. However, xylitol production is not quite desirable due to their slow production rate.

To improve the productivity of xylitol using the concentrated cells which were obtained by the centrifugation of cells grown in xylose medium or by the rapid accumulation of cells during fermentation process, the present invention developed the mutant cells having excellent yield for preparing xylitol and the optimal fermenting conditions for maximum xylitol production.

SUMMARY OF THE INVENTION

The object of the present invention is to provide novel mutant cells of *Candida parapsilosis*, which were deposited to Korean Culture Center of Microorganism with accession number KCCM-10088 on Oct. 21, 1996 under Budapest treaty, for preparing xylitol with high productivity.

The other object of the present invention is to provide the optimal fermentation conditions for maximum production of xylitol using mutant cells by controlling following conditions;

i) concentration of mutant cells by the centrifugation of cells grown on xylose medium or by the rapid accumulation of cells during fermentation process is 15~35 g/L;

ii) composition of medium for maximum production of xylitol consists of 5~12 (w/v) % of xylose, 0.2~2.0 (w/v) % of yeast extract, 0.2~2.0 (w/v) % of ammonium sulfate, 0.2~2.0 (w/v) % of $KH_2PO_4$ and 0.01~0.2 (w/v) % of $MgSO_4.7H_2O$;

iii) dissolved oxygen concentration in the medium is 0.1~5.0 (w/v) %;

iv) redox(reduction-oxidation) potential in the medium is 50~150 mV;

v) pH of cultivation medium is 4.5~5.5; and vi) temperature of cultivation is 27°~33° C.

DETAILED DESCRIPTION OF THE INVENTION

The mutant cells used for the present invention are isolated by following method.

A wild type of *Candida parapsilosis*(ATCC-21019) is spread and cultured to the yeast-malt extract(YM) medium containing 0.1% of nitroso methyl guanidine(NTG), and colony produced is separated by repeating separation method more than 3 times. The obtained colony is again spread and cultured to YM medium under UV illumination of 250~270 nm. Finally, growing colony is isolated and obtained as mutant cells. These mutant cells were deposited to Korean Culture Center of Microorganism with accession number KCCM-10088.

The following is fermentation method for producing xylitol using mutant cells.

Seed Culture

The frozen(−70° C.) mutant cells of *Candida parapsilosis* (KCCM-10088) are cultivated in 40~60 ml of YM medium (18~22 g/L of glucose, 4~5 g/L of pepton 2.5~3.5 g/L of yeast extract, 2.5~3.5 g/L of malt extract) at 28°~32° C. for 12~18 hours in 250 ml of flask. The cultured mutant cells are concentrated to 15~35 g/L by the centrifugation of cells grown xylose medium or by the rapid accumulation of cells during fermentation process to be used as the cells for producing xylitol in main culture.

Main Culture

The concentrated mutant cells obtained in following centrifugation method are used as the cells for main culture for producing xylitol The seed cells are cultivated in 3.0 % (w/v) xylose, 0.2~2.0 (w/v) % yeast extract, 0.2~2.0 (w/v) % $KH_2PO_4$, 0.2~2.0 (w/v) % $(NH_4)_2SO_4$ and 0.01~0.2 (w/v) % $MgSO_4.7H_2O$ at 28°~32° C. for 16~24 hours in a 10 L fermentor and then culture broth is centrifuged and concentrated.

The concentrated mutant cells are inoculated to the medium for maximum production of xylitol consisting of 10 (w/v) % xylose, 0.2~2.0 (w/v) % of yeast extract, 0.2~2.0 (w/v) % of ammonium sulfate, 0.2~2.0 (w/v) % of $KH_2PO_4$ and 0.01~0.2 (w/v) % of $MgSO_4.7H_2O$ in a 2.5 L fermentor. The main culture is cultivated at 100~500 rpm of agitation speed on pH 4.5~5.5 at 27°~33° C.

The concentrated mutant cells also obtained in following the rapied accumulation method of cells during fermentation process are used as the cells for main culture for producing xylitol. The cells are inoculated to a 5 L fermentor containing 3 L of medium containing 5~30 (w/v) % xylose which is fed during the fermentation, 0.2~2.0 (w/v) % yeast extract, 0.2~2.0 (w/v) % $KH_2PO_4$, 0.2~2.0 (w/v) % $(NH_4)_2SO_4$ and 0.01~0.2 (w/v) % $MgSO_4.7H_2O$. The main culture is cultivated at 100~600 rpm of agitation speed on pH 4.5~5.5 at 28°~32° C. for 16~24 hours.

The concentrated cells are rapidly achieved by maintaining a higher level (20~60%) of DO (dissolved oxygen) during the growth phase of fermentation and the DO concentration decrease to low level(0.8~1.2%) for effective xylitol production. Since xylitol is produced under microaerobic conditions, the change of DO from high level to low level is necessary for higher xylitol production.

The concentration of dissolved oxygen in the medium is very important for the production of xylitol, since the fermentation requires appropriate amount of oxygen. The optimal concentration of dissolved oxygen is 0.8~1.2 (w/v) % of dissolved oxygen, even though the fermentation can be performed under 0.1~5.0 (w/v) % of dissolved oxygen concentration. The concentration of dissolved oxygen can be controlled by redox potential level during fermentation. The desirable redox potential level is 50~100 mV, preferably 80~110 mV.

The fermentation process is preferably performed by fed batch process. After xylose was completely consumed in the medium, the amount of xylitol is measured by HPLC equipped with Sugar-Pak I column. The measured yield of xylitol is 65~85% of the biomass of xylose consumption and volumetric productivity is 1.7~4.7 g/L-hr, which are increased by 2~8 fold compared with conventional fermentation yield and productivity.

Finally, the fermentation medium is centrifuged for removing cells and other residue, and the supernatant is filtered and dialyzed for obtaining xylitol.

The present invention can be explained more specifically by following examples. However, the scope of the present invention cannot be limited to following examples.

EXAMPLE 1

The frozen(−70° C.) mutant cells of *Candida parapsilosis* (KCCM-10088) are cultivated in 50 ml of YM medium (18~22 g/L of glucose, 4~5 g/L of paptone 2.5~3.5 g/L of yeast extract, 2.5~3.5 g/L of malt extract) at 30° C. for 15 hours in 250 ml of flask. The seed cells are cultivated in 3.0% (w/v) xylose medium (0.2~2.0 (w/v) % yeast extract, 0.2~2.0 (w/v) % $KH_2PO_4$, 0.2~2.0 (w/v) % $(NH_4)_2SO_4$ and 0.01~0.2 (w/v) % $MgSO_4.7H_2O$ at 28°~32° C. for 16~24 hours in a 10 L fermentor and then culture broth is centrifuged and concentrated. The cultured mutant cells are concentrated to 20 g/L to be used as the cells for producing xylitol in main culture.

The concentrated mutant cells are inoculated to the medium for maximum production of xylitol consisting of 100 g/L of xylose, 5 g/L of yeast extract, 5 g/L of ammonium sulfate, 5 g/L of $KH_2PO_4$ and 0.2 g/L of $MgSO_4.7H_2O$. The main culture is cultivated at 450 rpm(oxygen transfer rate coefficient=60 $h^{-1}$) of agitation speed in a 2.5 L fermentor on pH 5.0 at 30° C. The concentration of dissolved oxygen is 1.0 (w/v) % of dissolved oxygen.

After 22 hours fermentation, the amount of xylitol is measured by HPLC equipped with Sugar-Pak I column. The obtained xylitol is 80 g/L and volumetric productivity is 3.6 g/L-hr.

EXAMPLE 2

The frozen(−70° C.) mutant cells of *Candida parapsilosis* (KCCM-10088) are cultivated in 50 ml of YM medium (18~22 g/L of glucose, 4~5 g/L of peptone 2.5~3.5 g/L of yeast extract, 2.5~3.5 g/L of malt extract) at 30° C. for 15 hours in 250 ml of flask. The seed cells are cultivated in 3.0% (w/v) xylose, 0.2~2.0 (w/v) % yeast extract, 0.2~2.0 (w/v) % $KH_2PO_4$, 0.2~2.0 (w/v) % $(NH_4)_2SO_4$ and 0.01~0.2 (w/v) % $MgSO_4.7H_2O$) at 28°~32° C. for 16~24 hours in a 10 L fermentor and then culture broth is centrifuged and concentrated. The cultured mutant cells are concentrated to 25 g/L to be used as the cells for producing xylitol in main culture.

The concentrated mutant cells are inoculated to the medium for maximum production of xylitol consisting of 100 g/L of xylose, 6 g/L of yeast extract, 6 g/L of ammonium sulfate, 6 g/L of $KH_2PO_4$ and 0.2 g/L of $MgSO_4.7H_2O$. The main culture is cultivated at 500 rpm(oxygen transfer rate coefficient=65 $h^{-1}$) of agitation speed in a 2.5 L fermentor on pH 5.0 at 30° C. The concentration of dissolved oxygen is 1.5 (w/v) % of dissolved oxygen.

After 18 hours fermentation, the amount of xylitol is measured by HPLC equipped with Sugar-Pak I column. The obtained xylitol is 81 g/L and volumetric productivity is 4.5 g/L-hr.

EXAMPLE 3

The frozen(−70° C.) mutant cells of *Candida parapsilosis* (KCCM-10088) are cultivated in 50 ml of YM medium (18~22 g/L of glucose, 4~5 g/L of peptone 2.5~3.5 g/L of yeast extract, 2.5~3.5 g/L of malt extract) at 30° C. for 15 hours in 250 ml of flask. The seed cells are cultivated in 3.0% (w/v) xylose medium (0.2~2.0 (w/v) % yeast extract, 0.2~2.0 (w/v) % $KH_2PO_4$, 0.2~2.0 (w/v) % $(NH_4)_2SO_4$ and 0.01~0.2 (w/v) % $MgSO_4.7H_2O$) at 28°~32° C. for 16~24 hours in a 10 L fermentor and then culture broth is centrifuged and concentrated. The cultured mutant cells are concentrated to 30 g/L to be used as the cells for producing xylitol in main culture.

The concentrated mutant cells are inoculated to the medium for maximum production of xylitol consisting of 100 g/L of xylose, 4 g/L of yeast extract, 4 g/L of ammonium sulfate, 4 g/L of $KH_2PO_4$ and 0.2 g/L of $MgSO_4.7H_2O$. The main culture is cultivated at 550 rpm(oxygen transfer rate coefficient=72 $h^{-1}$) of agitation speed in a 2.5 L fermentor on pH 5.0 at 30° C. The concentration of dissolved oxygen is 0.8 (w/v) % of dissolved oxygen.

After 20 hours fermentation, the amount of xylitol is measured by HPLC equipped with Sugar-Pak I column. The obtained xylitol is 85 g/L and volumetric productivity is 4.2 g/L-hr.

EXAMPLE 4

The frozen(−70° C.) mutant cells of *Candida parapsilosis* (KCCM-10088) are cultivated in 50 ml of YM medium (18~22 g/L glucose, 4~5 g/L pepton, 2.5~3.5 g/L yeast extract and 2.5~3.5 g/L malt extract) at 30° C. for 15 hours in 250 ml of flask and then 5 % (v/v) of culture broth is transferred to a 5 L fermentor containing 3 L of medium containing 30 (w/v) % xylose which is fed during the fermentation, 0.2~2.0 (w/v) % yeast extract, 0.2~2.0 (w/v) % $KH_2PO_4$, 0.2~2.0 (w/v) % $(NH_4)_2SO_4$ and 0.01~0.2 (w/v) % $MgSO_4.7H_2O$. The main culture is cultivated at 100–600 rpm of agitation speed on pH 4.5~5.5 at 28°~32° C. for 16~24 hours. Cultures are performed for the period that xylose is completely consumed.

Fed batch culture of xylose is carried out because of the inhibitory effect of high xylose concentration on xylitol production. The volume of fermentor increases form 2 L containing 300 g of xylose to 3 L containing 900 g of xylose by feeding twice of 500 ml containing 300 g. During the initial exponential phase of the fermentaion, the DO concentration is maintained at high level. After the cell concentration is reached at about 30 g/L for 20 h by the rapid accumulation of cells, the DO concentration is controlled in the ranges of 0.8~1.2% by adjusting agitaion speed(about 350~400 rpm). 240 g/L of xylitol obtained from 300 g/L of Xylose after 66 hours fermentation, which corresponds to the xylitol yield from xylose of 80%. Xylitol production rate of the fed-batch fermentation was increased to 3.63 g/L-hr due to the high concentration of cells.

EXAMPLE 5

Pilot plant experiments were carried out in a pilot-scale fermentor system (Korea Fermentor Co.).

The frozen(−70° C.) mutant cells of *Candida parapsilosis* (KCCM-10088) are cultivated in 75 ml of YM mddium (18~22 g/L, glucose, 4~5 g/L pepton, 2.5~3.5 g/L yeast extract and 2.5~3.5 g/L malt extract) at 30° C. for 15 hours in 500 ml of flask and then the culture broth is transferred to a 2.5 L fermentor containing YM medium of 1.5 L and cultivated at 28°~32° C. for 7~12 hours. This seed is inoculated to a 50 L fermentor containing fermentation medium of 30 L (5.0 % (w/v) xylose, 0.2~2.0 (w/v) % yeast extract, 0.2~2.0 (w/v) % $KH_2PO_4$, 0.2~2.0 (w/v) % $(NH_4)_2SO_4$ and 0.01~0.2 (w/v) % $MgSO_4 \cdot 7H_2O$) at 28~32° C. for 10~14 hours and then the culture broth of 30 L was transferred to a 400 L fermentor containing fermentation medium of 200 L and cultivated for 8 h. The seed of 200 L was inoculated to a 3,000 L main fermentor containing fermentation medium of 1,400 L. The temperature and pH of fermentors is controlled as 4.5~5.5 and 28~30° C., respectively. The DO concentration of seed fermentors is maintained above 20% and that of main fermentor is appropriately adjusted for effective xylitol production. Aeration rate is fixed to 0.5 vvm. Agitation speed gradually increases in the range of 40~130 rpm to maintain above DO of 20% during growth phase and is shifted in the range of 65~75 rpm during production phase which corresponds to the oxygen transfer coefficient of about 60 $h^{-1}$. The high concentrated cells are rapidly achieved by maintaining a higher level of DO during the growth phase of fermentation and the DO concentration decreases to low level for effective xylitol production. Since xylitol is produced under microaerobic conditions, the change of DO from high level to low level is necessary for higher xylitol production. The high production of xylitol form high xylose concentration is attempted by the rapid accumulation of cells and the use of DO and redox potential as control parameters.

Fed-batch culture of xylose is carried out with the initial concentration of about 170 g/L. The volume of fermentor is increased from 1,400 L containing xylose of 240 kg to 2,200 L containing xylose of 560 kg by twice feeding xylose of 160 kg (=400 L) at 31 h and 47 h, respectively. During the exponential growth phase of the fermentation, the DO concentration is maintained at high level. After the cell concentration was rapidly reached at about 20 g/L, the redox potential and DO are controlled in the ranges of 80~110 mV and 0.5~1.5%, respectively, by adjusting agitation speed. Total added concentration of xylose is 254.5 g/L and is completely consumed at 77 h. A final xylitol concentration of 208 g/L is obtained with a xylitol yield from xylose of 82%. Xylitol production rate increased to 2.69 g/L.h because of the increase of cell concentration.

COMPARATIVE EXAMPLE

The fermentation is carried out as the same manner of example 1 except that wild type of *Candida parapsilosis* (ATCC-21019) is used as the fermenting cell. The obtained xylitol is 52 g/L and volumetric productivity is 2.4 g/L-hr.

We claim:

1. A fermentation process for maximum production of xylitol using mutant cells *Candida parapsilosis* deposited to Korean Culture Center of Microorganisms with accession number KCCM-10088 comprising the steps of:

i) fermenting xylose medium with the mutant cells wherein
   a) the mutant cell concentration by centrifugation of mutant cells grown on xylose medium or by rapid accumulation of the cells during fermentation is 15~35 g/L;
   b) the medium consists of 5~12 (w/v) % of xylose, 0.2~2.0 (w/v) % of yeast extract, 0.2~2.0 (w/v) % of ammonium sulfate, 0.2~2.0 (w/v) % of $KH_2PO_4$ and 0.01~0.2 (w/v) % of $MgSO_4 \cdot 7H_2O$;
   c) dissolved oxygen concentration in the medium is 0.1~5.0 (w/v) %;
   d) redox (reduction-oxidation) potential in the medium is 50~150 mV;
   e) pH of the fermentation medium is 4.5~5.5; and
   f) temperature of fermentation is 27°~33° C.;

ii) removing the mutant cells and other residue from the fermentation medium; and iii) separating and recovering xylitol from the fermentation medium of step (ii).

2. The fermentation process according to claim 1, wherein dissolved oxygen concentration in the medium is 0.8~1.2 (w/v) % and redox potential in the medium is 80~110 mV.

3. The fermentation process according to claim 1, wherein the mutant cells used for fermentation are prepared by cultivating frozen (−70° C.) *Candida parapsilosis* (accession number KCCM-10088) in 40~60 ml of YM medium (18~22 g/L of glucose, 4~5 g/L of pepton 2.5~3.5 g/L of yeast extract, 2.5~3.5 g/L of malt extract) at 28°~32° C. for 12~18 hours.

4. The novel mutant cells of *Candida parapsilosis* (KCCM-10088).

5. A method of isolating *Candida parapsilosis* mutants having the genotype of *C. parapsilosis* (KCCM-10088) comprising the steps of:

i) spreading and culturing a wild type *Candida parapsilosis* (ATCC-21019) on yeast-malt extract (YM) medium containing 0.1% nitrosomethylguanidine (NTG);

ii) isolating the produced colonies at least three times on YM medium;

iii) spreading and culturing the colonies of step (ii) on YM medium under UV illumination of 250~270 nm; and iv) isolating the growing colonies.

* * * * *